United States Patent
Barry

(10) Patent No.: US 11,219,476 B2
(45) Date of Patent: Jan. 11, 2022

(54) SURGICAL SYSTEMS, KITS AND METHODS FOR SETTING BONE SEGMENTS

(71) Applicant: Mark A. Barry, Las Vegas, NV (US)

(72) Inventor: Mark A. Barry, Las Vegas, NV (US)

(73) Assignee: Mark A. Barry, Las Vegas, NV (US)

( * ) Notice: Subject to any disclaimer, the term of this patent is extended or adjusted under 35 U.S.C. 154(b) by 0 days.

(21) Appl. No.: 16/573,868

(22) Filed: Sep. 17, 2019

(65) Prior Publication Data
US 2020/0008845 A1    Jan. 9, 2020

Related U.S. Application Data

(63) Continuation of application No. 15/641,701, filed on Jul. 5, 2017, now Pat. No. 10,426,529.

(51) Int. Cl.
*A61B 17/72*    (2006.01)
*A61B 17/86*    (2006.01)

(52) U.S. Cl.
CPC ........ *A61B 17/725* (2013.01); *A61B 17/7208* (2013.01); *A61B 17/7283* (2013.01); *A61B 17/8605* (2013.01); *A61B 17/8685* (2013.01)

(58) Field of Classification Search
CPC . A61B 17/72; A61B 17/7208; A61B 17/7216; A61B 17/7225; A61B 17/7233; A61B 17/7241; A61B 17/725
USPC .................................................. 606/62–64
See application file for complete search history.

(56) References Cited

U.S. PATENT DOCUMENTS

| | | | |
|---|---|---|---|
| 4,169,470 A | 10/1979 | Ender et al. | |
| 5,545,165 A | * | 8/1996 | Biedermann ...... A61B 17/7032 606/261 |
| 6,053,918 A | 4/2000 | Spievack | |
| 6,517,541 B1 | 2/2003 | Sesic | |
| 7,066,937 B2 | 6/2006 | Shluzas | |
| 8,979,846 B2 | 3/2015 | Thakkar | |

(Continued)

FOREIGN PATENT DOCUMENTS

CN    204379417 U    6/2015
DE    102011109209 A1    2/2013

OTHER PUBLICATIONS

Depuy Synthes; Titanium/stainless steel elastic nail system. For elastic stable intrmedullary nailing (ESIN); 64 pages; retrieved from the internet (http://synthes.vo.llnwd.net/o16/LLNWMB8/INT%20Mobile/Synthes%20International/Product%20Support%20Material/legacy_Synthes_PDF/DSEM-TRM-0115-0290-2_LR.pdf) on Oct. 17, 2017.

(Continued)

*Primary Examiner* — Eduardo C Robert
*Assistant Examiner* — Christina Negrelli-Rodriguez
(74) *Attorney, Agent, or Firm* — Shay Glenn LLP

(57) ABSTRACT

An intramedullary nail system is provided with at least one resilient, elongate nail body configured to extend axially along a medullary bone cavity, and at least one bone anchor. The bone anchor includes a distal bone engagement portion configured to secure the anchor to a bone, a proximal nail engagement portion configured to receive a portion of the nail body therethrough, and a tightening mechanism configured to move from a movable state in which the nail body may slide axially and rotate through the engagement portion and a fixed state in which the nail body is prevented from moving relative to the engagement portion. Methods of use and surgical kits are also provided.

10 Claims, 5 Drawing Sheets

(56) References Cited

U.S. PATENT DOCUMENTS

| | | |
|---|---|---|
| 10,426,529 B2 | 10/2019 | Barry |
| 2001/0034524 A1 | 10/2001 | Bales |
| 2005/0277934 A1* | 12/2005 | Vardiman .......... A61B 17/7083 606/914 |
| 2007/0100342 A1 | 5/2007 | Green et al. |
| 2007/0276382 A1* | 11/2007 | Mikhail ............. A61B 17/1739 606/62 |
| 2008/0154264 A1 | 6/2008 | Wack et al. |
| 2009/0157078 A1 | 6/2009 | Mikol |
| 2010/0042157 A1* | 2/2010 | Trieu ................ A61B 17/7004 606/255 |

OTHER PUBLICATIONS

Ellis et al.; A comparison of locked versus nonlocked enders rods for length unstable pediatric femoral shaft fractures; Journal of pediatric orthopaedics; 31(8); pp. 825-833; Dec. 1, 2011.
Smith & Nephew Orthopaedics; Treatment of humeral tibial, and femoral fractures with ender nails; pp. 7118-0271, 16 pages; (Product discription and Technique discription); Memphis, TN; Jun. 1995.

* cited by examiner

SURGICAL SYSTEMS, KITS AND METHODS FOR SETTING BONE SEGMENTS

CROSS REFERENCE TO RELATED APPLICATIONS

This application is a continuation of U.S. application Ser. No. 15/641,701, filed Jul. 5, 2017, which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

This disclosure is in the field of setting segments of bone. It generally relates to implanting resiliently flexible intramedullary pins, nails or rods into a medullary cavity of a bone. More specifically, this disclosure relates to systems, kits and methods in which the intramedullary pins, nails or rods are anchored to the bone.

BACKGROUND

Intramedullary nails and the like have been used by surgeons for many decades to set bone segments for healing, such as when setting a fractured femur or radius. Terms used for these types of devices include intramedullary nails, rods, pins, Nancy nails, Ender nails, Elastic Stable Intramedullary Nails (ESINs) and Titanium Elastic Nails (TENs.) These devices typically extend along at least a portion of a medullary cavity of a bone in a generally axial direction. Some intramedullary nails are rigid, fill all or most of the medullary cavity of a bone, and can include interlocking parts. Other nails are much more slender and flexible, and fill only a small portion of the cross-section of the medullary cavity. Flexible nails provide the benefit of entering the medullary cavity of a bone away from the growth plate in children with fractures and other bone destabilizing conditions, as opposed to rigid nails which generally traverse, and thus may injure the growth plate.

An example of a flexible type of intramedullary nail is provided by U.S. Pat. No. 4,169,470 issued Oct. 2, 1979, to Josef Ender et al. Ender et al. teach the use of a nail having a length predetermined for a particular application according to an individual patient's anatomy and fracture pattern. In some procedures, more than one nail is used to set a bone. As such, a large variety of nail lengths must be on hand during a surgical procedure using such nails. Additionally, estimating or pre-measuring the correct nail length is frequently challenging, particularly with displaced fractures. In some procedures, the surgeon may not know the desired length until a nail is inserted and it is determined to be too long or too short for the particular application. This results in some nails being discarded, and can require a large inventory of nails to be on hand for every procedure. For example, a variety of nails are often provided in 1 cm increments. Smith & Nephew lists 18 different nail lengths that must be stocked. This is multiplied by 3 or 4 when various incremental diameters are needed, such as 3.0, 3.5, 4.0 and 4.5 mm. In some procedures a trial pin is first placed and its insertion depth is measured to determine the proper nail length for the procedure. This approach requires an extra step, and in some cases the replacement nail does not follow the same path through the bone segments as does the trial pin. This can require additional attempts to place the nail, or leave a nail in place that is not the ideal length.

Ender et al. disclose nails that include a slot at one end. Ender et al. teach that these slots can be used to place an extraction hook used for later removal of the nail. However, surgeons have subsequently used these slots to pass a bone screw therethrough for securing the end of the nail to the bone, as shown in FIG. 1. This method of securing is prone to screw thread stripping, such as when an operator over-tightens a screw when desiring more secure fixation, or when bone thickness or density is insufficient to hold the bone screw. Since the nail slot is elongated, in some instances the bone screw may not completely eliminate axial movement of the nail after implantation. The screw can toggle, causing loosening, breakage or pull-out of the screw. These events can cause the fracture to shift post-operatively, leading to sub-optimal results which may require revision.

Additionally, the nail end and bone screw head sit on top of the outer bone surface and can interfere with surrounding tissue, causing prominent, palpable and painful implants, and or other undesirable side effects. This is done to prevent the end of the nail from being buried and covered by healing bone, making extraction difficult. Resulting pain from such an implant prominence can lead to a patient refusing to bend a joint until the implant is removed, adding further delay to patient recovery.

Another example of a flexible intramedullary nail is provided by U.S. Pat. No. 8,979,846 issued Mar. 17, 2015, to Navin Thakkar. Thakkar teaches the use of a universal length nail that may be cut to the desired length after implantation. With the excess length of the nail protruding from the bone, a surgeon can cut the nail at a distance of about 1 cm from the external surface of the bone at the entry point. This leaves about 1 cm of the nail protruding from the bone until such time that the nail is removed, which can cause undesirable side effects such as those described above in reference to Ender.

In some embodiments disclosed by Thakkar, neither end of the flexible nail is anchored to the bone. In other embodiments, multiple nails are placed through the greater trochanter of a femur and anchored thereto using a proximal fixation device. Such a procedure is not performed these days. Today, whenever a rod is sent through the greater trochanter, it is virtually always a single, larger (8-10 mm) diameter rod in a person over age 13 (close to skeletal maturity), where violation of the greater trochanteric growth plate is not an issue. If the Thakkar construct were used to anchor nails to the greater trochanter, it is not clear that the construct would prevent the hooked ends of the nails from migrating outwardly from the bone.

DePuy Synthes Trauma, a division of Synthes GmbH, currently markets an elastic stable intramedullary nailing (ESIN) system having a Titanium Elastic Nail (TEN) or Stainless Steel Elastic Nail (STEN) Like the Thakkar nails, the Synthes nails are designed to be cut to length in situ. In some implementations, an externally threaded end cap is provided to reduce irritation of the protruding nail and help anchor a nail to the bone. The end cap is inserted over the cut end of the nail and threaded into the bone obliquely. It appears that this arrangement inhibits a fracture from fore-shortening but does not provide any rigid fixation, and may not prevent the fractured bone segments from separating as the nail may slide out of the end cap. There is also no rotational control provided. At the date of this patent application filing, Synthes provides more information on the above systems in a surgical technique guide at: http://synthes.vo.llnwd.net/o16/LLNWMB8/INT%20Mobile/Synthes%20International/Product%20Support%20Material/legacy_Synthes_PDF/DSEM-TRM-0115-0290-2_LR.pdf.

FIG. 2 of the present disclosure is a three-panel x-ray of a spiral fracture that was set with two prior art flexible intramedullary nails. FIG. 2A shows the untreated displaced fracture. This type of spiral fracture pattern is "length unstable." FIG. 2B shows the fracture immediately postoperatively. FIG. 2C shows the fracture postoperatively after some time has elapsed and the protruding ends of the intramedullary nails have migrated out of the bone, allowing the bone fracture to foreshorten. This case illustrates the need for good anchoring of the entry site ends of the nails.

Indicated benefits of many prior art systems are quite limited. In light of the many challenges during surgery and postoperatively outlined above, what is needed and is not provided by the prior art are systems and methods that provide improved bone fixation with flexible intramedullary nails, including in skeletally immature children.

SUMMARY OF THE DISCLOSURE

This disclosure is in the field of setting segments of bone. It generally relates to implanting resiliently flexible intramedullary pins, nails or rods into a medullary cavity of a bone. More specifically, this disclosure relates to systems, kits and methods in which the intramedullary pins, nails or rods are anchored to the bone. The innovations disclosed herein solve the drawbacks found in the prior art described above in the Background Section.

According to aspects of the disclosure, an intramedullary nail system is provided in which there is a rigid link between the nail and an anchor. The link may be perpendicular in two planes. This arrangement enhances purchase and minimizes nail migration and postoperative bone displacement, resulting in more assured maintenance of the position of the destabilized bone.

According to aspects of the disclosure, an intramedullary nail system is provided in which there is reduced risk of bone screw stripping. An anchor or "tulip" bed cavity in the bone may be prepared with a countersink tool of fixed depth (equal to the tulip height). Screw insertion will stop when the tulip is screwed down flush with the cortical surface of the bone.

According to aspects of the disclosure, an intramedullary nail system is provided in which the exact nail length can be conveniently determined. After nail insertion, the proper length is measured relative to the tulip position and the nail is cut or broken off accordingly. In some embodiments, the excess nail is cut or otherwise removed several millimeters past the tulip, providing extra grip on the nail for eventual removal. The nail end is countersunk into the tulip channel and a set screw is placed to secure the nail in the tulip channel.

According to aspects of the disclosure, an intramedullary nail system is provided in which the bone anchor facilitates bone entry access. After the bone anchor is placed, an access drill may be advanced into the tulip channel paralleling the axis the nail will assume. This obviates the need for an awl and can control the nail entry direction into the bone and bone entry hole size more accurately.

Unlike many of the prior art systems, the systems, methods and surgical kits disclosed herein may be used on persons under the age of 13.

According to aspects of the disclosure, an intramedullary nail system is provided with a resilient, elongate nail body configured to extend axially along a medullary bone cavity and to occupy a portion of the cavity. The intramedullary nail system is also provided with a bone anchor. The bone anchor comprises a distal bone engagement portion configured to secure the anchor to a bone, a proximal nail engagement portion configured to receive a portion of the nail body therethrough, and a tightening mechanism. The tightening mechanism is configured to move from a movable state in which the nail body may slide axially and rotate through the engagement portion, and a fixed state in which the nail body is prevented from moving relative to the engagement portion.

In some embodiments of the intramedullary nail system, at least a portion of the nail body is curved. As an example, a curved portion of the nail body may have a radius of curvature between 150 and 300 cm to achieve segmental bone fixation. The distal bone engagement portion of the anchor may include external threads configured to engage a bone. In some embodiments, the distal bone engagement portion of the anchor extends generally perpendicular to the nail body. The elongate nail body may be provided with a series of weakened portions configured to allow the nail body to be severed at one of the weakened portions. In some embodiments, the series of weakened portions comprises a series of grooves spaced apart from one another at 1 cm increments. The nail body may comprise a diameter of no more than 5 mm.

According to aspects of the disclosure, a surgical kit is provided with a plurality of nail bodies as described above, and a plurality of bone anchors as describe above. In some embodiments of the surgical kit, the plurality of bone anchors comprises anchors having distal bone engagement portions of more than one length. In some embodiments of the surgical kit, the plurality of nail bodies comprises nail bodies having diameters of more than one size. The surgical kit may include one or more countersink tools configured to drill a countersink in a bone such that the proximal portion of a bone anchor will be flush with an outer surface of the bone when the matching sized anchor is implanted therein.

According to aspects of the disclosure, a method of intramedullary bone fixation comprises installing a bone anchor in a bone, sliding a resilient, elongate nail body longitudinally into the bone through the installed bone anchor and along a medullary cavity of the bone to occupy a portion of the cavity, and tightening a mechanism on the bone anchor. The mechanism on the bone anchor may be tightened such that the mechanism moves from a movable state in which the nail body may slide axially and rotate through the engagement portion and a fixed state in which the nail body is prevented from moving relative to the bone anchor.

In some embodiments of the method of intramedullary bone fixation, the method includes creating a countersink cavity in the bone prior to installing the bone anchor in the bone. The countersink cavity may be sized and shaped to receive the similarly sized and shaped bone anchor therein. In some embodiments, the installed bone anchor protrudes from an outer surface of the bone to a minimal degree so as to obviate overlying soft tissue irritation, such as no more than 1 mm. In some embodiments, the bone anchor protrudes 0 to 2 mm. The method may further comprise removing an excess length from a protruding end of the nail body after the nail body has been installed in the bone. The nail body may be slid into a final position and the bone anchor mechanism may be tightened after the excess length is removed from the nail body. In some embodiments, the installed nail body protrudes from an outer surface of the bone no more than 1 mm. In some embodiments, the nail body protrudes about 2-3 mm.

In some embodiments of the method, the method includes performing the installing, sliding and tightening steps on a plurality of bone anchors and nail bodies installed into the same bone. The nail body may comprise a diameter of no more than 5 mm. In some embodiments, the nail body occupies only a portion of a lateral cross section of the medullary cavity of the bone.

BRIEF DESCRIPTION OF THE DRAWINGS

The novel features of the disclosure are set forth with particularity in the claims that follow. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

Figure 1:
FIG. 1 is an x-ray image showing two prior art flexible intramedullary nails implanted into a bone with the proximal ends anchored to the bone with bone screws.
Figures 2A, 2B, 2C:
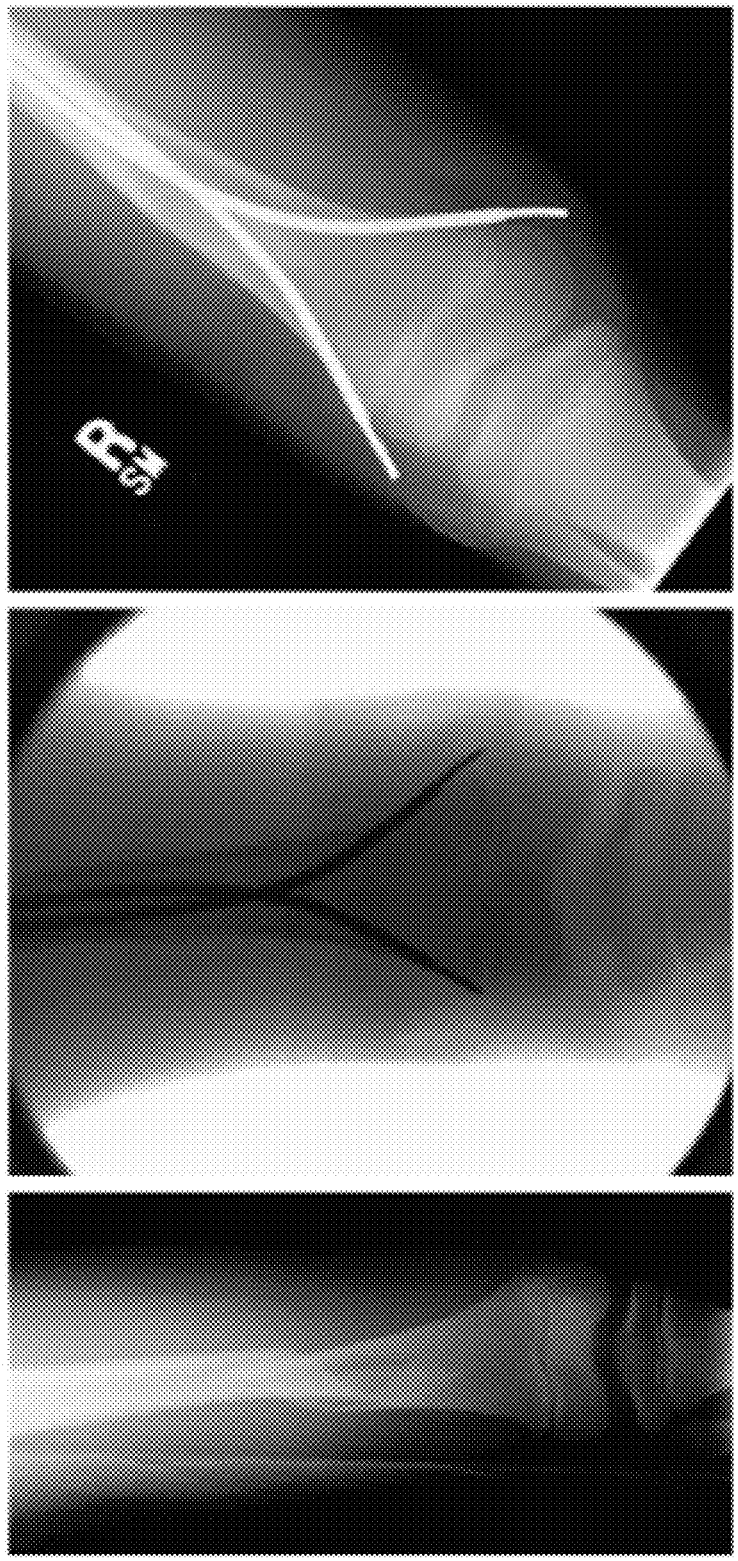
FIG. 2A is an x-ray image showing an untreated spiral fracture.
FIG. 2B is an x-ray image showing the spiral fracture of FIG. 2A immediately after being set with two prior art flexible intramedullary nails.
FIG. 2C is an x-ray image showing the treated spiral fracture of FIG. 2B after some time has elapsed and the proximal ends of the prior art intramedullary nails have migrated out of the bone.
Figure 3:
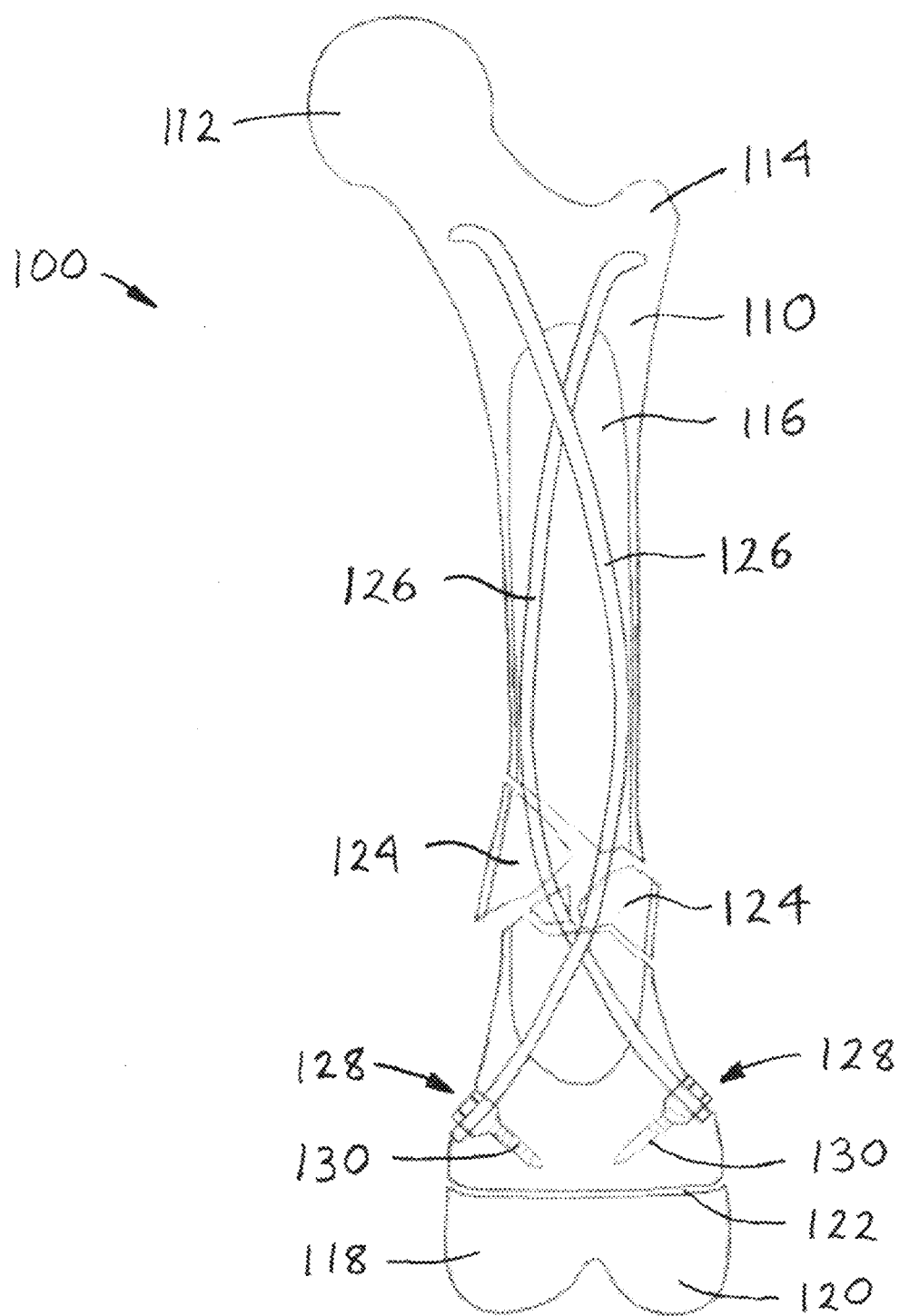
FIG. 3 is a frontal view of a femur showing an exemplary bone fixation system 100 constructed and implanted according to aspects of the present disclosure.

Referring to FIG. 3, an exemplary bone fixation system 100 constructed and implanted according to aspects of the present disclosure is shown. In this exemplary embodiment, system 100 is shown implanted in a femur 110. Femur 110 includes a head 112, greater trochanter 114, medullary cavity 116, medial condyle 118, lateral condyle 120 and lower physis or growth plate 122. Also depicted in FIG. 3 are various bone fragments 124 located at a fracture site on femur 110. While bone fixation system 100 is discussed below relative to setting a fractured femur, the same principles apply when using system 100 to set bone segments of a tibia, radius, ulna, clavicle or other bones.

In this exemplary embodiment, system 100 includes two resiliently flexible nail bodies 126. Nail bodies 126 are depicted in FIG. 3 implanted in femur 110 in a mirror-like opposing orientation that stably fixes femur 110 in position for healing. Nail bodies 126 are generally arcuate in shape, and are constructed such that they exhibit spring-like properties when they are flexed. In some embodiments, nail bodies 126 have an overall radius of curvature between 150 and 300 cm when in their natural, un-flexed state. A single nail body 126 may be used in some bone fixation procedures, but when at least two nail bodies 126 are used together such as shown in FIG. 3, their opposing spring forces counterbalance one another to provide stable bone fixation. In some embodiments, the ends of each nail body 126 are embedded in the cancellous bone at each end of the femur while the mid-portion of each nail body 126 resides in the medullary cavity 116 and presses against the cortical bone walls of the cavity, as shown in FIG. 3. With a pair of curved nail bodies 126 positioned in opposite orientations, the nail bodies 126 resiliently press upon opposite sides of medullary cavity 116 to provide balanced forces that resist the bone portions from bending, rotating or moving towards or away from one another.

Figure 4:
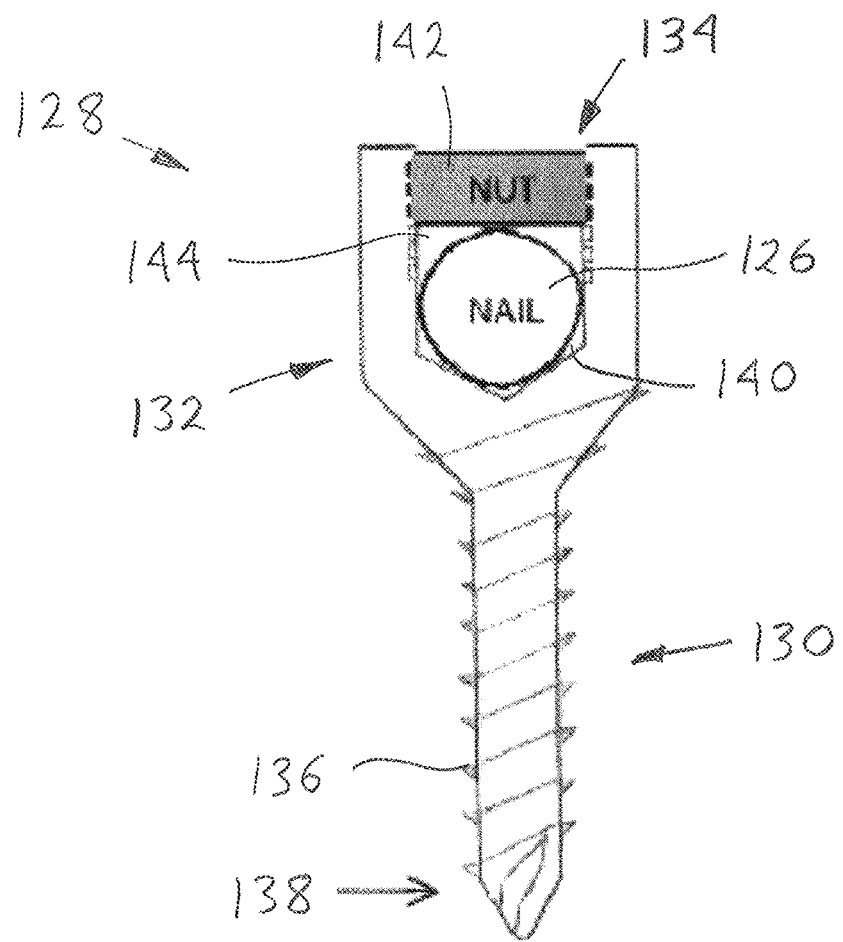
FIG. 4 is an enlarged side view showing and exemplary bone anchor 128 constructed according to aspects of the present disclosure.

To further fix femur 110 from movement, an anchor 128 is provided at the entry site end of each nail body 126. As best seen in FIG. 4, each anchor 128 is provided with a distal bone engagement portion 130, a proximal nail engagement portion 132, and a tightening mechanism 134. In some embodiments, bone anchor 128 is constructed similar to a vertebral pedicle screw designed to connect to a spinal rod.

Distal bone engagement portion 130 of bone anchor 128 is configured to secure anchor 128 to bone. In the exemplary embodiment shown in FIG. 4, distal bone engagement portion 130 comprises external threads 136. Distal tip 138 may be configured such that it is self-drilling and or self-tapping. In other embodiments (not shown), the distal bone engagement portion may be provided with a Morse taper, a molly bolt, a spline, a wedge, a cylinder, a spike or other suitable configuration so that it may be threadably engaged, press-fit, compress-fit, glued, or otherwise affixed to bone. In some embodiments, bone cutting and or bone material removal features may be added to the tapered and or cylindrical portions of the proximal anchor head to allow the anchor to be self-countersinking.

The entry site or proximal nail engagement portion 132 is configured to receive a portion of the nail body therethrough. In the exemplary embodiment shown in FIG. 4, a transverse channel 140 is provided through the proximal end of anchor 128 perpendicular to bone engagement portion 130. Channel 140 is sized to receive nail body 126. In some embodiments, the width of channel 140 is only slightly larger than the diameter of nail body 126 in order to firmly secure the nail. In some embodiments, channel 140 extends outwardly to the proximal end of anchor 128 as shown such that nail body 126 may be placed into channel 140 from an axial direction. In other embodiments (not shown), channel 140 may only open on opposite sides of anchor 128 such that nail 126 is inserted only from a radial direction and its entire circumference is constrained by the walls of channel 140.

In some embodiments (not shown), channel 140 is not perpendicular to bone engagement portion 130 but rather has another predetermined angle suitable for setting the trajectory of nail body 126 within medullary cavity 116. It should be noted that in such embodiments, it may be necessary to install the anchor in a specific orientation such that the desired channel angle is achieved. In other embodiments (not shown), a pivoting or poly-axial connection is provided between proximal nail engagement portion 132 and distal bone engagement portion 130 such that the orientation of portion 132 may be adjusted in one or more directions relative to portion 130. In some embodiments, this connection may be locked down after adjustment, and in others it may remain free to move in certain directions post-operatively even though nail body 126 is constrained from axial movement within channel 140.

Tightening mechanism 134 is configured to move from a movable state in which nail body 126 may slide axially and rotate through engagement portion 132, and a fixed state in which nail body 126 is prevented from moving relative to engagement portion 132. In the exemplary embodiment shown in FIG. 4, tightening mechanism 134 comprises a nut or set screw 142 provided with external threads around its circumference for engaging with an internally threaded bore 144. Bore 144 connects with transverse channel 140. The top surface of nut 142 may be provided with a recess for receiving a tool such as an Allen wrench so that nut 142 may be tightened down onto nail body 126 to secure it against the bottom of channel 140 as shown. In some embodiments (not shown), a lock nut may be inserted into bore 144 and tightened down against nut 142 to ensure it does not work loose post-operatively. In other embodiments (not shown), a cam lock, bayonet connection, latch, lever or other suitable mechanism may be used instead of nut 142 to secure nail body 126 relative to engagement portion 132.

Referring to FIGS. 3 and 4, one exemplary method of implanting bone fixation system 100 into a fractured bone according to aspects of the present disclosure will be described. Many variations of this exemplary technique are contemplated in this disclosure, depending on the particular injury or deformity being treated and subject to the judgment of the performing surgeon.

FIG. 3 depicts a femur having a distal fracture with multiple bone fragments 124. In this exemplary procedure, two nail bodies 126 are inserted in a retrograde direction, although in other implementations (not shown), one or more than two nail bodies 126 may be used, and they may be inserted in an antegrade direction. The patient may be placed in a supine position on a fracture table and the legs abducted. In some implementation, a small incision 2 to 4 cm long is made adjacent to each nail entry point above the lower physis (growth plate) 122 (e.g. one lateral and one medial.) A countersink tool (not shown) is used having the shape of the bone anchor 128 of FIG. 4, or just the shape of the cylindrical and tapered proximal nail engagement portion 132 thereof. The countersink tool is used to create a cavity in the bone into which bone anchor 128 may be fully recessed. A bone anchor 128 is then threaded into the base of each cavity created by the countersink tool. As previously described, the tip of bone anchor 128 may be configured to be self-drilling and or self-tapping. The interior and or exterior of bone anchor 128 may be provided with features (not shown) configured to mate with a bone anchor driving tool (not shown) so that each bone anchor 128 may be threaded into place as shown in FIG. 3, with each anchor 128 fully recessed within the bone 110 or protruding only a minimal amount. In some implementations, a portion of bone anchor 128 protrudes no more than 1 mm above the outer surface of the bone 110. In some embodiments, the bone anchor protrudes 0 to 2 mm.

With one or more bone anchors 128 installed in the bone 110, a nail body 126 may be inserted into the bone 110 through the proximal nail engagement portion 132 of bone anchor 128. In some implementations nail bodies 126 may be inserted into the bone 110 before bone anchors 128 are installed. However, by installing bone anchors 128 first, the cortical bone around the nail entry points can be preserved. With prior art nail systems that do not install an anchor first, the cortical bone around the entry point can be damaged by the nail as it is being manipulated down the length of the bone and being used to align bone segments, thereby making the entry hole through the cortical bone too large and leaving too little bone material to fully anchor the nail in the preferred position. In contrast, by installing bone anchors 128 before implanting nail bodies 126 therethrough according to aspects of the disclosure, the bone anchors can be used as secure leverage points through which the nail bodies and bone segments can be manipulated without damaging the cortical or cancellous bone around the entry points.

In some implementations, nut 142 may be installed in bone anchor 128 (as shown in FIG. 4) before the anchor is implanted into the bone, or after anchor 128 is implanted but before nail body 126 is inserted through the anchor. This arrangement allows bone anchor 128 to better define the initial trajectory that nail body 126 should take as it enters the bone, and allows the surgeon to better use anchor 128 as a leverage point as bone segments may need to be manipulated into position with nail body 126. In some implementations, a drill bit may be passed through the proximal nail engagement portion 132 of bone anchor 128 after it has been implanted in order to create a transverse path through the bone on one or both sides of the anchor for the nail body 126 to follow.

After the insertion site(s) have been prepared, such as described above, nail body(ies) 126 may be inserted through their respective insertion site. Each nail 126 passed through the cortical bone where bone anchor 128 has been or will be placed, through the adjacent cancellous bone and or into medullary cavity 116. In some embodiments, nail body 126 is provided with a leading tip having a tighter radius of curvature than the overall radius of curvature of the nail, as shown in FIG. 3. As nail 126 is passed through the medullary cavity 116, it may be used to align/knit together bone fragments 124 and or the lateral and or rotational orientation of the distal portion of bone 110 relative to its proximal portion. The distal tip of each nail 126 is then passed into the cancellous bone material at the opposite end of bone 110 from the entry site as shown in FIG. 3, preferably avoiding the growth plates at that end of the bone. Once each nail body 126 is in its desired position, bone anchors 128 are installed as previously described, if they were not previously installed before nail insertion. Nut 142 of each anchor 128 may now be tightened down against each nail body 126, as shown in FIG. 4.

At various points or continuously throughout the procedure, an imaging system such as fluoroscopy may be used to help the surgeon ensure that anchor(s) 128, nail body(ies) 126, and segments and or fragments 124 of bone 110 are in the desired positions. The surgeon at this point may cut off the excess length of each nail body 126 that protrudes outwardly from its associated bone anchor 128. Cutters and or pliers (not shown) may be used for this purpose. In some implementations, the surgeon may stop short of fully inserting each nail body 126 into bone 110 before cutting off the excess portion. For example, a surgeon can stop 1 cm short of full nail insertion, cut off all but 1 cm of the protruding end of nail 126 outwardly protruding from anchor 128, and then continue pushing the nail into bone 110 up to 1 cm further such that very little nail body 126 protrudes from bone anchor 128. This arrangement can give the surgeon additional room to maneuver the cutting or bending instruments yet ensure that a minimal or no portion of the nail body 126 protrudes from the outer surface of bone 110 after the procedure has been completed. In some embodiments, the nail body protrudes about 2-3 mm. This is just enough for the surgeon to feel the underside of the nail to lift it out of the tulip. More protruding would likely lead to too much bone excavation with removal of the nail.

Figure 5:
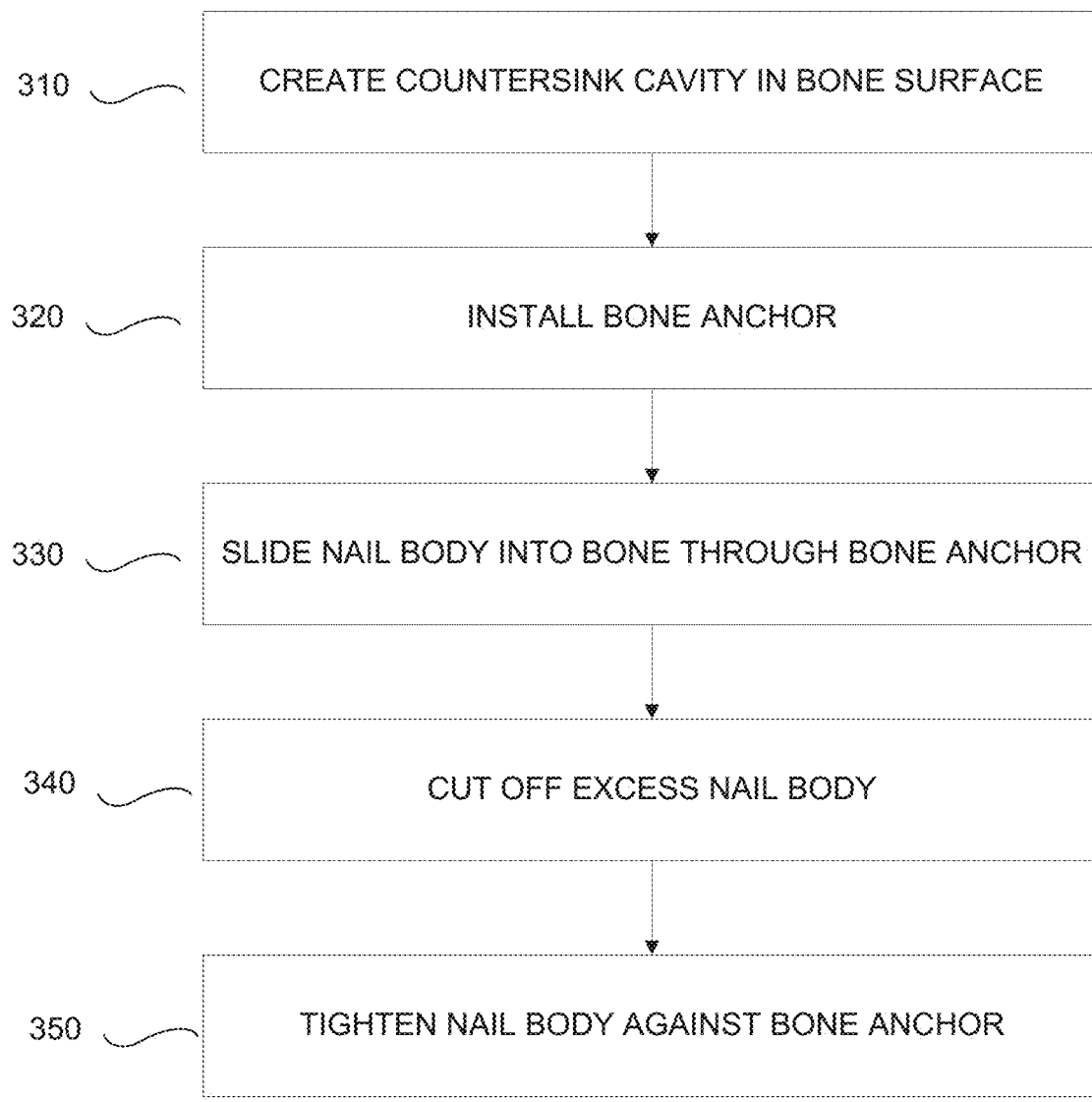
FIG. 5 is a flow chart illustrating an exemplary bone fixation method according to aspects of the present disclosure.

Referring to FIG. 5, a summary of aspects of the above exemplary method is provided. In step 310 a countersink cavity is created in the surface of the bone using a countersink tool. A bone anchor is then installed in the countersink cavity in step 320. With the bone anchor installed in the bone, the anchor can be used as a guide as a nail body is slid through the anchor into the bone, as shown in step 330. In step 340, excess length of the nail body outwardly protruding from the bone anchor may be cut off. Once the nail body is in place, the nail body can be tightened against the bone anchor in step 350. This prevents the nail body from sliding longitudinally or rotating with respect to the anchor, which in turn inhibits bone segments from moving after they have been set by the nail body.

Each of the above steps may be performed for all of the anchors and intramedullary nails being installed before moving to the next step, all steps may be performed for a first anchor and nail pair before moving to the next pair, or a combination thereof. In some implementations, the order of the steps may be varied and/or some steps may be omitted.

In some implementations, the bone anchor(s) and the nail body(s) are removed in a later procedure after the bone defect has sufficiently healed. To remove the implanted hardware, the surgeon may loosen or remove the nut from the bone anchor, grab the proximal end of the nail body with pliers and pull the nail body out through the bone anchor. The bone anchor is then unscrewed and removed from the bone.

The inventive systems, kits and methods disclosed herein may be used for a wide variety of indications, some of which may not be treatable with prior art flexible nail systems. For example, the disclosed systems may be used to treat bony defects, such as tumors, leg lengthening or shortening. These indications actually need a greater degree of length and rotationally stable fixation, which the disclosed systems provide. Other indications include fractures that are length unstable, are located close to the end of a nail (e.g. the distal femoral fracture depicted in FIG. 3), or where greater rotational and angular control is needed. The disclosed systems may obviate the need for a second nail in special situations, such as osteogenesis imperfecta. The systems may also be used in reconstruction, such as osteotomies having rotational, shortening and or angular components.

The terms and expressions employed herein are used as terms and expressions of description and not of limitation, and there is no intention, in the use of such terms and expressions, of excluding any equivalents of the features shown and described or portions thereof. In addition, having described certain implementations in the present disclosure, it will be apparent to those of ordinary skill in the art that other implementations incorporating the concepts disclosed herein can be used without departing from the spirit and scope of the invention. The features and functions of the various implementations can be arranged in various combinations and permutations, and all are considered to be within the scope of the disclosed invention. Accordingly, the described implementations are to be considered in all respects as illustrative and not restrictive. The configurations, materials, and dimensions described herein are also intended as illustrative and in no way limiting. Similarly, although physical explanations have been provided for explanatory purposes, there is no intent to be bound by any particular theory or mechanism, or to limit the claims in accordance therewith.

What is claimed is:

1. An intramedullary nail system comprising:
    a resilient, elongate nail body configured to extend axially along a medullary bone cavity and to occupy a portion of the cavity, the nail body having a longitudinal axis that comprises a curved portion, the curved portion comprising a diameter of no more than 5 mm, an overall radius of curvature of between 150 and 300 cm to achieve segmental bone fixation and configured to exert a lateral spring force against a wall of the medullary bone cavity after the nail body has been implanted in the cavity, the elongate nail body comprising a leading tip having a tighter radius of curvature than the overall radius of curvature; and
    a bone anchor comprising:
        a distal bone engagement portion configured to secure the anchor to a bone;
        a proximal head portion having a diameter larger than a diameter of the distal bone engagement portion;
        a proximal nail engagement portion located on the larger diameter proximal head portion and configured to receive a portion of the nail body therethrough; and
        a tightening mechanism configured to move from a movable state in which the nail body may slide axially and rotate through the proximal nail engagement portion and a fixed state in which the nail body is prevented from moving relative to the proximal nail engagement portion.

2. The intramedullary nail system of claim 1, wherein the curved portion of the nail body has a radius of curvature sufficient to achieve intramedullary bone stabilization.

3. The intramedullary nail system of claim 1, wherein the distal bone engagement portion of the anchor comprises external threads configured to engage a bone.

4. The intramedullary nail system of claim 1, wherein the distal bone engagement portion of the anchor extends generally perpendicular to the nail body.

5. The intramedullary nail system of claim 1, wherein the elongate nail body can be cut to a desired length in vivo.

6. A surgical kit comprising:
    a plurality of nail bodies as recited in claim 1; and
    a plurality of bone anchors as recited in claim 1.

7. The surgical kit of claim 6, wherein the plurality of bone anchors comprises anchors having distal bone engagement portions of more than one length.

8. The surgical kit of claim 6, wherein the plurality of bone anchors comprises nail engagement portions of more than one size.

9. The surgical kit of claim 6, wherein the plurality of nail bodies comprises nail bodies having diameters of more than one size.

10. The surgical kit of claim 6, further comprising a countersink tool configured to drill a countersink in a bone such that the proximal portion of a bone anchor will be approximately flush with an outer surface of the bone when the anchor is implanted therein.

\* \* \* \* \*